United States Patent
Quist

[11] Patent Number: 5,843,058
[45] Date of Patent: Dec. 1, 1998

[54] ABSORBENT STRUCTURE AND AN ABSORBENT ARTICLE WHICH INCLUDES THE ABSORBENT STRUCTURE

[75] Inventor: Magnus Quist, Floda, Sweden

[73] Assignee: SCA Hygiene Products AB, Harryda, Sweden

[21] Appl. No.: 553,509

[22] PCT Filed: May 20, 1994

[86] PCT No.: PCT/SE94/00477

§ 371 Date: Nov. 30, 1995

§ 102(e) Date: Nov. 30, 1995

[87] PCT Pub. No.: WO94/28839

PCT Pub. Date: Dec. 22, 1994

[30] Foreign Application Priority Data

Jun. 9, 1993 [SE] Sweden .................................. 9301972

[51] Int. Cl.$^6$ .................................................. A61F 13/15
[52] U.S. Cl. ........................................... 604/369; 604/378
[58] Field of Search ..................... 604/359, 369, 604/368, 372, 378, 383, 385.1, 304, 307; 521/140

[56] References Cited

U.S. PATENT DOCUMENTS

| | | | |
|---|---|---|---|
| 3,122,141 | 2/1964 | Crowe, Jr. | 604/369 |
| 3,156,242 | 11/1964 | Crowe, Jr. | 604/369 |
| 3,371,667 | 3/1968 | Morse | 304/369 |
| 3,834,389 | 9/1974 | Dulle . | |
| 4,061,145 | 12/1977 | DesMarais | 604/363 |
| 4,381,782 | 5/1983 | Mazurak et al. | 604/369 |
| 4,423,101 | 12/1983 | Willstead . | |
| 5,439,458 | 8/1995 | Noel et al. | 604/368 |
| 5,445,604 | 8/1995 | Lang | 604/304 |

FOREIGN PATENT DOCUMENTS

| | | | |
|---|---|---|---|
| 0299122A1 | 1/1989 | European Pat. Off. . | |
| 0 299 122 A1 | 3/1989 | European Pat. Off. | 604/369 |
| 1 450 201 | 9/1976 | United Kingdom | 604/369 |
| 1450201 | 9/1976 | United Kingdom . | |
| 1 585 628 | 3/1981 | United Kingdom | 604/369 |
| 1585628 | 3/1981 | United Kingdom . | |
| 2 098 993 | 12/1982 | United Kingdom | 604/369 |
| 2098993 | 12/1982 | United Kingdom . | |
| 2 279 013 | 12/1994 | United Kingdom | 604/369 |
| WO 94/28839 | 12/1994 | WIPO | 604/369 |

*Primary Examiner*—Robert A. Clarke
*Attorney, Agent, or Firm*—Burns, Doane, Swecker & Mathis, LLP

[57] ABSTRACT

An absorbent structure in an absorbent article, such as a sanitary napkin, tampon, panty protector, incontinence guard, diaper and the like, which is produced by including in the absorbent structure a polymeric foam having cells which were initially essentially closed and which has been worked so as to open said cells, and the structure has obtained liquid take up properties. The foam has a density between 0.01–0.5 g/cm$^3$. The material has porperties which are effective in achieving the function for which the product is intended. The foam may be formed as a sheet and the sheet can be made very thin and light, with a surface weight of between 10–500 g/m$^2$, and the article will therefore exhibit good comfort properties to the wearer and requires only a small amount of material for its manufacture.

14 Claims, 4 Drawing Sheets

ABSORBENT STRUCTURE AND AN ABSORBENT ARTICLE WHICH INCLUDES THE ABSORBENT STRUCTURE

BACKGROUND OF THE INVENTION

The present invention relates to an absorbent structure in an absorbent article, such as a sanitary napkin, tampon, panty protector, incontinence guard, diaper and the like.

Many different types of absorbent articles of this kind are known to the art. The absorbent body of such products is conventionally produced by dry-defibering cellulose pulp in roll, bale or sheet form for instance, and converting the cellulose pulp in fluffed form to a pulp mat, sometimes admixed with so-called superabsorbents in the pulp mat, these superabsorbents being polymers which are capable of absorbing many times their own weight of water or body fluid.

The pulp body is often compressed, with the intention of enhancing its fluid-dispersion properties and also to lower the bulk of the pulp body and therewith to obtain a product which is as compact as possible.

The absorbent body may include other constituents, for instance to improve the fluid-receiving properties or the liquid-dispersion properties of the absorbent body, or to increase its coherency and its ability to resist deformation in use.

With the majority of sanitary products, it is desired that the article shall be thin and pliable, partly to enable the article to be worn as discretely as possible and partly so that the article will feel as comfortable as possible to the wearer. Another problem is the so-called rewetting problem. By rewetting is meant that body fluid that has already been absorbed by the sanitary article is pressed back into contact with the wearer's skin by external forces, for instance when the wearer sits down. It is a general desire that the surface of the article which lies proximal to the user will remain as dry as possible.

With regard to absorbent articles, it is desired to reduce the amount of material in the article, so as to reduce commensurately the amount of waste that occurs when the used product is thrown away. It is also desired to enable the article to be manufactured from biologically degradable material.

Other problems concerning absorbent articles reside partly in their total absorption capacity, and also in that the articles often leak long before their total absorption capacity has been utilized to the full. Among other things, this is because the discharged body fluid is unable to penetrate into the absorbent material and be dispersed to hitherto unused regions of the article quickly enough, but instead leaks from the sides of the sanitary napkin, diaper or incontinence guard. The ability of the materials used in such articles to disperse the absorbed fluid through-out the whole of the absorbent body is thus an important feature of such articles.

A very large part of the production plant employed in the manufacture of such sanitary articles is normally comprised of defibrating equipment, pneumatic conveyor systems and mat-forming equipment. This equipment often constitutes serious source of error and faults in the production plants. Additionally, this equipment is often followed by equipment for compressing the finished pulp mat or the finished sanitary article.

EP 0,044,624 and U.S. Pat. No. 4,394,930, among others, describe polymeric foam having superabsorbent properties for use in absorbent articles. The use in absorbent articles of polymeric foam which lacks superabsorbent properties is described in EP 0,163,150 and EP 0,299,122, among others. Although these absorbent articles obtain good properties, the manufacturing process is relatively complicated and the materials thus produced are relatively expensive.

U.S. Pat. No. 3,834,389 describes how a polyurethane foam, for instance, can be chemically reticulated in order to open up the common walls between adjecent cell, which enhances the absorbancy of the foam.

OBJECTS AND SUMMARY

An object of the present invention is to provide an absorbent article having an absorbent structure of the kind defined in the introduction which will afford a high degree of comfort to the wearer, among other things with regard to thinness and suppleness. It is also desired to reduce the amount of material consumed in manufacture. The article will preferably have good absorbent properties and low rewetting tendencies. It is also desired that an absorbent article of the kind defined in the introduction can be manufactured in a simplified manner. These desiderata are satisfied by means of the present invention, in that the absorbent structure includes a foamed polyolefin material having a density of 0.01–0.5 $g/cm^3$ and cells which are initially essentially closed but which have been opened to increase the fluid take up properties, e.g. the sorbing properties, of the material.

BRIEF DESCRIPTION OF THE DRAWINGS

The invention will now be described in more detail with reference to exemplifying embodiments thereof and also with reference to the accompanying drawings, in which.

DETAILED DESCRIPTION OF THE PREFERRED EMBODIMENTS

Figure 1:
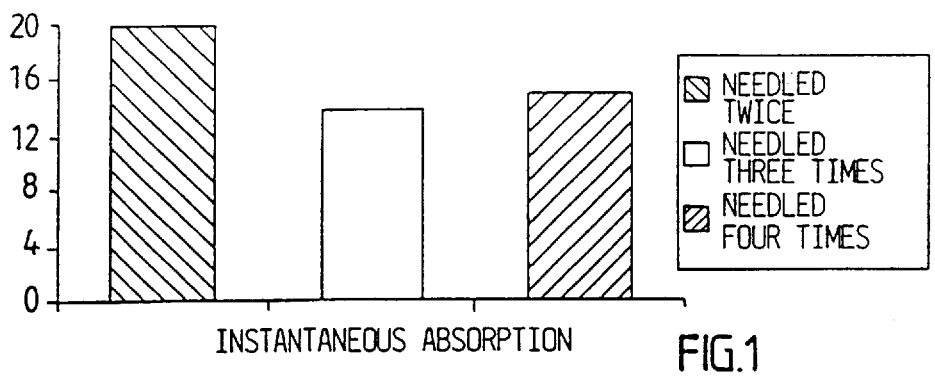
FIG. 1 illustrates how the instantaneous absorption of the material is influenced by the number of times the material has been perforated by needling.

As before mentioned, comfort properties, such as softness and suppleness, and absorption properties such as absorption capacity, absorption rate and rewetting, are all important properties of a material used in the manufacture of a sanitary article. The fluids concerned include urine, menstruation blood, blood and wound fluids.

The object of the present invention is to provide an absorbent structure in an absorbent article, such as a sanitary napkin, tampon, panty protector, incontinence guard, diaper and the like, which will afford a high degree of comfort to the wearer, with regard to thinness and suppleness among other things. Another object is to reduce the amount of material consumed in manu-facture. The material used in the article will also preferably have good absorption properties and exhibit low rewetting tendencies. A further object is to simplify the process of manufacture. A ready-to-use absorbent material in roll form which can be used without needing to defiber the material will eliminate the requirement of the aforesaid defibering equipment, pneumatic conveyor system and mat-forming equipment.

The aforesaid objects have been solved in accordance with the invention, by including in the absorbent structure a sheet which comprises a foamed polymeric material having cells which were initially essentially closed and which have been opened so as to increase the fluid take up properties of the material. The foam has a density of 0.01–0.5 $g/cm^3$.

By perforating the foamed polymeric material by means of a needling process, the material is given absorption properties which render said material highly suited for use as an absorbent material in the majority of sanitary articles. Perforation of the material opens the cells in the polymeric material which were initially closed, so as to form open structures having fluid take up properties.

The material can be perforated mechanically by needling in the manner used to produce needled felt for instance, or with the aid of water jets under high pressure in the manner used to obtain spunlace nonwoven material.

The aforesaid methods of working the material shall be seen solely as examples, and it will be understood that other methods can be applied to achieve corresponding results. An example of other conceivable methods is one in which the material is perforated by electromagnetic radiation or with the aid of laser radiation.

The aforesaid polymeric foam has been found to provide a highly efficient absorbent material and it has also been found possible to use this absorbent material in sanitary articles. The foamed sheet can be made very thin, therewith obviating the need to further compress the product. However, the sheet will permit further compression, if this is desirable in respect of some product application. A suitable sheet surface weight is 10–500 $g/m^2$.

The polymeric foam can be produced from both thermoplastic and thermosetting resins. The thermoplastics that can be used include simple polyolefins, for instance polyethylene, which is an inexpensive and commercially abundant material. The thermosetting materials that can be used include polyurethanes.

Foamed material can be produced from these plastics, for instance by blowing air into the molten plastic bath during manufacture, or by foaming the material through fermentation by gas formation resulting from chemical reactions in the polymeric material.

When polyolefins are used to apply the invention, the absorbent article can be made very light in weight, and therewith economically beneficial. It is possible to reduce the weight of the absorbent body to 5–10% of the weight of a corresponding absorbent body made of conventional cellulose material, while retaining the requisite absorption capacity of said body.

The amount of waste represented by the absorbent article can also be reduced, by using bioplastics, which are renewable and biologically degradable. Examples of such materials are polysaccharide, polylactides and polyhydroxy alkanoids, and mixtures of such polymers. Other types of degradable polymers can also be used.

When polyolefins are used to apply the invention, it is necessary to modify the original hydrophobic surface to a hydrophilic surface. This surface modification can be achieved in different ways, for instance by adding surfactants, by plasma treatment, by corona treatment, by copolymerization, by admixing other polymers, or by other methods. When a surfactant is added to a material according to the invention, its properties can be adjusted with regard to absorption rate, absorption capacity, rewetting tendencies, etc.

A material according to the invention can be combined with conventional absorbent materials, for instance cellulose pulp, or with superabsorbent material, to form an absorbent structure. An example of one such material is a so-called SAP-tissue which is comprised of two layers of cellulose wadding with an intermediate layer of superabsorbent. A suitable surface weight with regard to SAP-tissue is 50–100 $g/m^2$, divided over two layers of cellulose wadding with a surface weight of 10–20 $g/m^2$ and a layer of superabsorbent having a surface weight of 40–80 $g/m^2$. Such an absorbent structure obtains an improved instantaneous absorption and better rewetting properties than an absorbent structure having solely a polymeric foam according to the invention.

Investigation of Material Properties

The following test methods and test equipment were applied to evaluate the properties of the material.

Method 1—Determining Instantaneous Absorption

A sample body measuring 65×200 mm was punched from the material, weighed and then placed onto a flat supporting surface. 15 ml of sample liquid (0.9% NaCl-solution) was applied to the wetting point of the sample body. The time taken to absorb all liquid was measured in seconds. This time period was expressed as instantaneous absorption.

Method 2—Determining Instantaneous Rewetting

A sample body measuring 65×200 mm was punched from the material, weighed and then placed on a flat supporting surface. 15 ml of sample liquid (0.9% NaCl-solution) were applied to the wetting point of the sample body. A filter paper was then placed on top of the wetting point and subjected to a load of 5 kPa for 15 seconds. The filter paper was weighed before and after applying the load and the difference calculated. The result, expressed in grams, was expressed as instantaneous-rewetting.

Method 3—Determining Rewetting

This method was applied to determine rewetting after a load had been applied over a given time period. A sample body measuring 65×200 mm was punched from the material, weighed and then placed on a flat supporting surface. 15 ml of sample liquid (0.9% NaCl-solution) were applied to the wetting point of the sample body. A plexiglass plate having a larger surface than the sample body was then placed on top of the body and subjected to a load of 5 kPa for 5 minutes. The plexiglass plate was then removed and a filter paper was placed on the wetting point and subjected to a load of 5 kPa for 15 seconds. The filter paper was weighed before and after subjecting the body to load and the result, expressed in grams, was expressed as rewetting.

Method 4—Manufacture of Sample Bodies for Determining the Surfactant Influence

A sample body measuring 65×200 mm was punched from the material, weighed and then placed in a container containing an aqueous surfactant solution for 5 minutes. The sample body was then removed from the container and allowed to drain for 5 minutes, whereafter the sample body was subjected to a load of 10 kPa for 5 minutes. The sample body was then dried in the absence of load at a temperature of 40°–60° C. for 10–15 hours. The sample body was then tested according to one of the Methods 1–3.

The Influence of the Needling Degree

Instantaneous absorption of a surfactant-treated polyethylene foam according to the invention, having a thickness of 4 mm, a surface weight of 80 g/m$^2$, and a density of 0.02 g/cm$^3$, and which had been needled a different number of times was determined. The results were determined in accordance with Method 1.

A Inventive material, needled twice.

B Inventive material, needled three times.

C Inventive material, needled four times.

It will be seen from FIG. 1 that material which had been needled three times had a slightly quicker instantaneous absorption than the remaining materials.

Instantaneous-rewetting and rewetting of a surfactant-treated polyethylene foam according to the invention having a thickness of 4 mm, a surface weight of 40 g/m$^2$ and a density of 0.02 g/cm$^3$, and which had been needled a different number of times was determined. The results were determined according to Method 2 and Method 3.

A Inventive material, needled twice.

B Inventive material, needled three times.

C Inventive material, needled four times.

Figure 2:
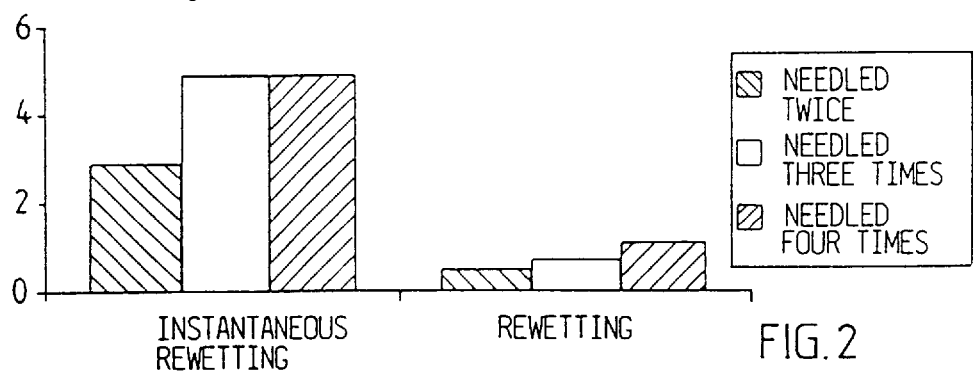
FIG. 2 shows how instantaneous-rewetting and rewetting of the material is influenced by the number of times that it has been perforated by needling.

It will be seen from FIG. 2 that instantaneous-rewetting and rewetting increases slightly when the number of needlings are increased.

Influence of Material Thickness on Instantaneous Absorption

Figure 3:
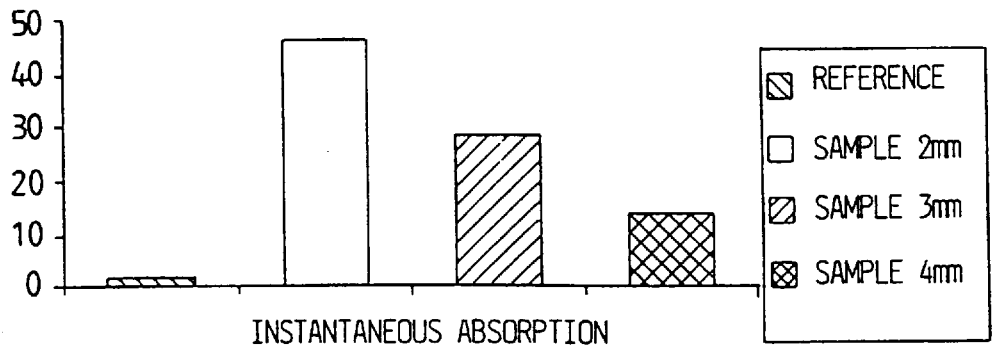
FIG. 3 shows how the instantaneous absorption of the material is influenced by its thickness, and also shows a comparison with a reference product.

Instantaneous absorption of a surfactant-treated polyethylene foam according to the invention, having a density of 0.02 g/cm$^3$, and which had been needled three times, was determined. The reference product comprised a conventional cellulose pulp mat. The results are shown in FIG. 3. The results were determined according to Method 1.

A Pulp mat thickness 4 mm, density 0.12 g/cm$^3$.

B Inventive material, thickness 2 mm.

C Inventive material, thickness 3 mm.

D Inventive material, thickness 4 mm.

It will be seen from FIG. 3 that material constructed in accordance with the invention has quicker instantaneous absorption when the thickness of the material increases.

Influence of Material Thickness on Instantaneous-Rewetting and Rewetting

Figure 4:
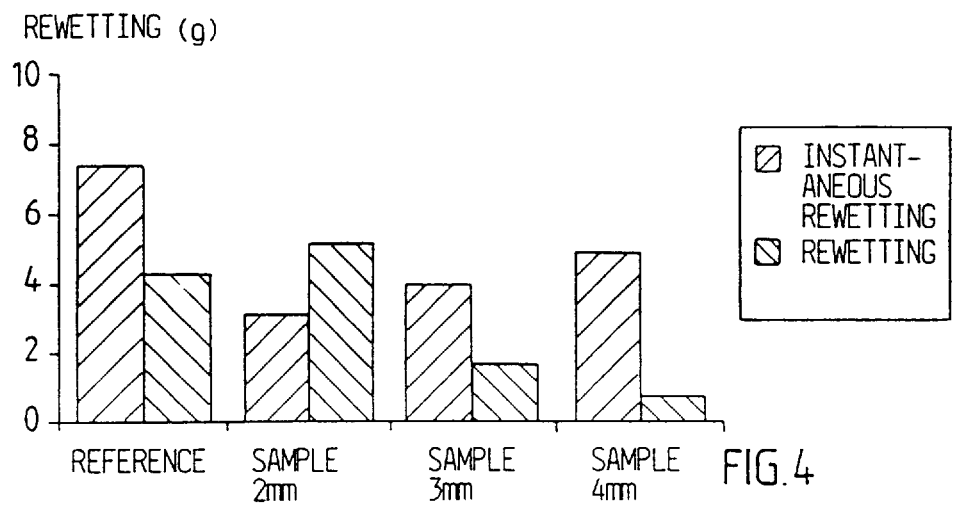
FIG. 4 shows how instantaneous-rewetting and rewetting of the material is influenced by its thickness, and also shows a comparison with a reference product.

Instantaneous-rewetting and rewetting of surfactant-treated polyethylene foams according to the invention having different thickness, 2–4 mm, and a density of 0.02 g/cm$^3$, and which had been needled three times, was determined. The reference product comprised a conventional cellulose pulp mat. The results are shown in FIG. 4. The results were determined according to Method 2 and Method 3.

A Pulp mat thickness 4 mm, density 0.12 g/cm$^3$.

B Inventive material, thickness 2 mm.

C Inventive material, thickness 3 mm.

D Inventive material, thickness 4 mm.

It will be seen from FIG. 4 that instantaneous-rewetting of inventive material increases slightly when the material thickness increases within the range of 2–4 mm. Rewetting is lower than rewetting of the reference product, in all cases. It will also be seen that rewetting of material constructed in accordance with the invention decreases when the material thickness increases within the range 2–4 mm. Rewetting is comparable with or lower than with the reference product, in all cases.

Surfactant Admixture and Its Influence on Rewetting

Figure 5:
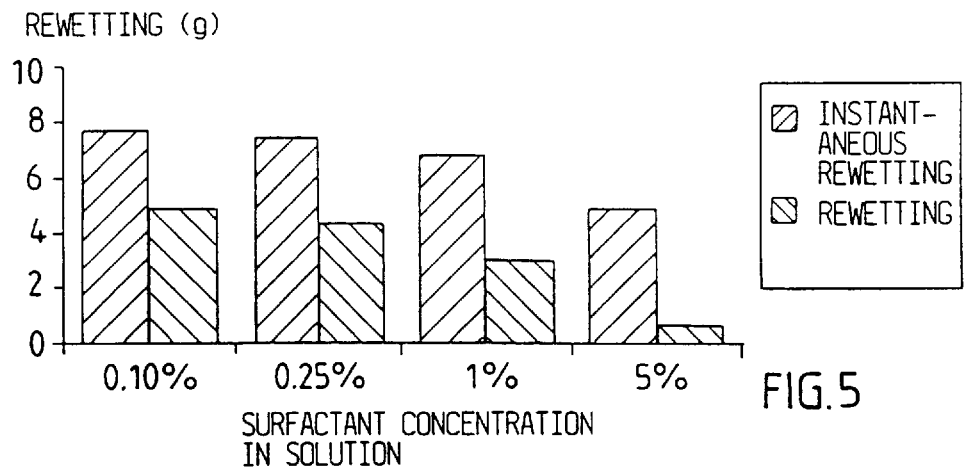
FIG. 5 shows how instantaneous-rewetting and rewetting of the material is influenced by the surfactant concentration of the solution used to surface-modify the material.

Instantaneous-rewetting and rewetting of a surfactant-treated polyethylene foam according to the invention, having a density of 0.02 g/cm$^3$, and a thickness of 4 mm, and which had been needled three times and treated with surfactant solutions of various concentrations is shown in FIG. 5. The samples were manufactured in accordance with Method 4, and the results were determined according to Method 2 and Method 3.

A Inventive material, 0.1% surfactant solution.

B Inventive material, 0.25% surfactant solution.

C Inventive material, 1% surfactant solution.

D Inventive material, 5% surfactant solution.

It will be seen from FIG. 5 that instantaneous-rewetting and rewetting decreases when the surfactant concentration increases within the range given.

Rewetting Compared with Conventional Products

Figure 6:
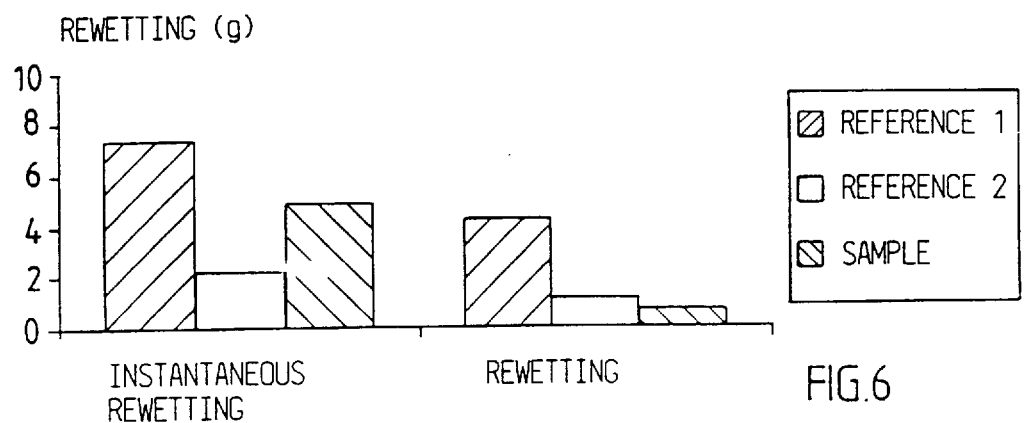
FIG. 6 illustrates a comparison between instantaneous-rewetting and rewetting of an inventive material and various reference products.

Instantaneous-rewetting and rewetting for a surfactant-treated polyethylene foam according to the invention, having a density of 0.02 g/cm$^3$, a thickness of 4 mm, and which had been needled three times, and also for conventional pulp pads were determined according to Method 2 and Method 3. The conventional products comprised different cellulose-fibre pulp mats. The results are shown in FIG. 6.

A Pulp mat thickness 10 mm, density 0.08 g/cm$^3$.

B Pulp mat thickness 4 mm, density 0.2 g/cm$^3$.

C Material constructed in accordance with the invention.

It will be seen from FIG. 6 that the instantaneous-rewetting and rewetting values of the inventive material are comparable with or lower than with the reference products. Reference 2 has the best instantaneous-rewetting value, while an inventive material has the best rewetting value.

Figure 7:
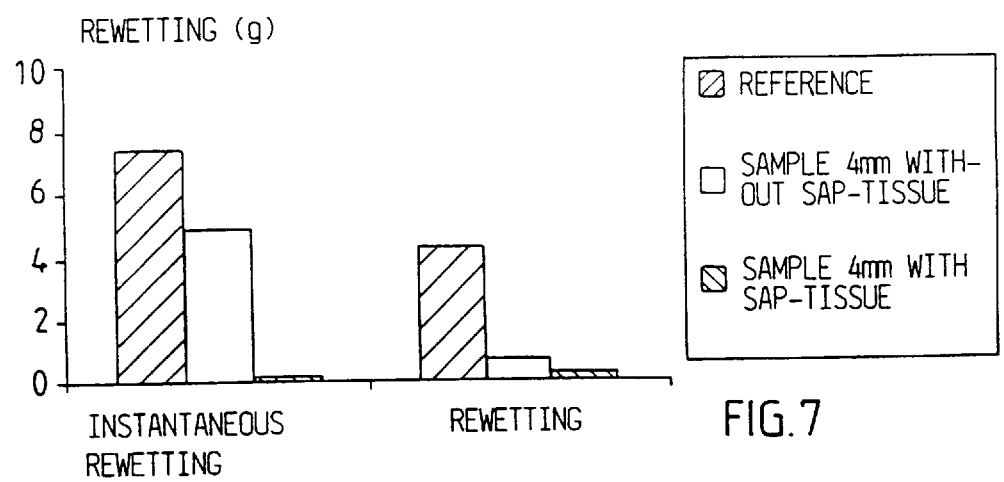
FIG. 7 illustrates a comparison between instantaneous-rewetting and rewetting of an inventive material with and without SAP-tissue and a reference product.
Figure 8:
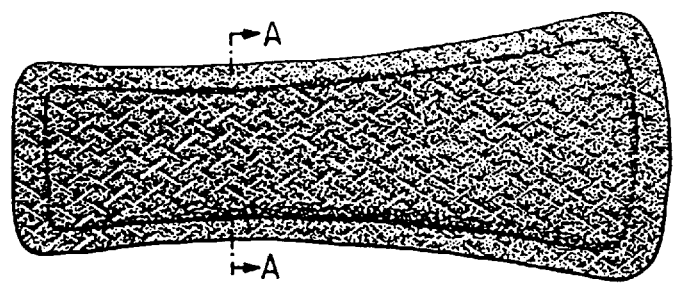
FIG. 8 is a top view of one example of an inventive absorbent article; the section A—A is shown in FIGS. 9 and 10.

Rewetting of an Absorbent Body Incorporating SAP-Tissue, as Compared with Conventional Products Instantaneous-rewetting and rewetting of a surfactant-treated polyethylene foam according to the invention, having a density of 0.02 g/cm$^3$, a thickness of 4 mm, and which had been needled three times and tested with and without the inclusion of SAP-tissue and of a conventional pulp pad were determined according to Method 2 and Method 3. The SAP-tissue was comprised of two layers of 15 g/m$^2$ cellulose wadding and an intermediate 40 g/m$^2$ layer of super-absorbent. The conventional product comprised a pulp mat of cellulose fibres. The results are shown in FIG. 7.

A Pulp mat thickness 10 mm, density 0.08 g/cm$^3$.

B Inventive material, 4 mm without SAP-tissue.

C Inventive material, 4 mm+70 g/m$^2$ SAP-tissue.

It will be seen from FIG. 7 that inventive material which included SAP-tissue exhibited better instantaneous rewetting values and rewetting values than the reference product.

Density and Surface Weight

The material can be made very thin, down to a thickness of about 1 mm, and consequently it is unnecessary, in many cases, to further compress the material prior to its use in an absorbent article. A suitable density is 0.01–0.5 g/cm$^3$, preferably 0.01–0.2 g/cm$^3$, and more preferably 0.02–0.1 g/cm$^3$. A suitable surface weight is 10–500 g/m$^2$, preferably 20–200 g/m$^2$ and more preferably 40–100 g/m$^2$.

Description of an Exemplifying Embodiment

Figure 9:
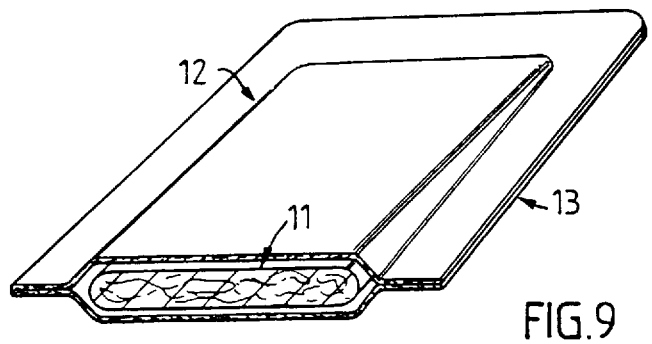
FIG. 9 is a cross-sectional view of an example of the schematic construction of an absorbent article constructed in accordance with one embodiment of the invention.

FIG. 9 is a cross-sectional view of an inventive sanitary napkin according to a first embodiment. The napkin includes, conventionally, an absorbent body 11 which is enclosed between a liquid-permeable top sheet 12, which is suitably comprised of perforated plastic film, nonwoven material or like material, and which lies proximal to the wearer in use, and a liquid-impervious bottom sheet 13. The sheets 12 and 13 have parts which extend beyond the absorbent body 11, and are mutually joined at these parts. The bottom sheet 13 is comprised of a suitable plastic material, for instance polyethylene. Naturally, the top sheet and the bottom sheet may be formed from other known materials, within the scope of the invention.

The absorbent body 11 consists solely of one single layer. This layer may be comprised of inventive material and optionally 0–10% superabsorbent material. A suitable density range with regard to the absorbent body 11 is 0.01–0.1 g/cm$^3$, while a suitable surface weight is 20–100 g/m$^2$.

Figure 10:
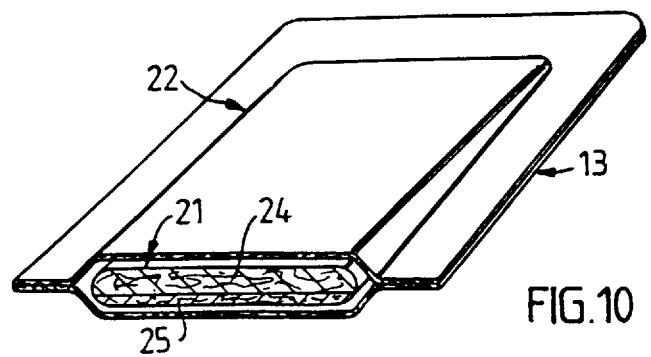
FIG. 10 is a cross-sectional view of an example of the schematic construction of an absorbent article according to one embodiment of the invention in combination with SAP-tissue.

FIG. 10 is a cross-sectional view of a sanitary napkin according to a second embodiment of the invention, this embodiment differing from the embodiment illustrated in FIG. 9, in that the absorbent body 21 includes two layers 24 and 25. The layer 24 may be comprised of material according to the invention, and optionally also 0–10% superabsorbent material. The layer 25 may be comprised of so-called SAP-tissue, which consists of two layers of cellulose wadding, about 15 g/m$^2$, and a layer of superabsorbent material, about 40 g/m$^2$, placed between said two layers of cellulose wadding. A suitable density range with regard to the layer 24 is 0.01–0.1 g/cm$^3$, while a suitable surface weight is 20–100 g/m$^2$.

It will be understood that the invention is not restricted to the described and illustrated exemplifying embodiments thereof and that other embodiments are conceivable within the scope of the concept of the invention.

I claim:

1. An absorbent article, comprising:

an absorbent structure, the absorbent structure consisting solely of a foamed polyolefin material having a density of 0.1–0.5 g/cm$^3$, and cells of said foamed polyolefin material that initially were closed have been opened by mechanical treatment to increase fluid take up properties of the material;

a liquid-permeable top sheet; and an essentially liquid-impervious bottom sheet;

wherein the absorbent structure is enclosed between said liquid-permeable top sheet and said essentially liquid-impervious bottom sheet.

2. The absorbent article according to claim 1, wherein said structure has the form of a sheet having a surface weight of 10–500 g/m$^2$.

3. The absorbent article according to claim 1, wherein the polyolefin material includes 0.1–25 percent by weight of surfactant.

4. The absorbent article according to claim 1, wherein the polyolefin material includes 1–50 percent by weight of superabsorbent material.

5. The absorbent article according to claim 1, wherein the structure includes a separate layer of some other absorbent material.

6. The absorbent article according to claim 5, wherein the separate layer of absorbent material includes cellulose and superabsorbent material.

7. The absorbent article according to claim 1, wherein said structure has the form of a sheet having a surface weight of 20 to 200 g/m$^2$.

8. The absorbent article according to claim 1, wherein said structure has the form of a sheet having a surface weight of 40 to 80 g/m$^2$.

9. The absorbent article according to claim 1, wherein said treatment has been effected by perforating the polymeric material by needling.

10. The absorbent article according to claim 1, wherein the treatment has been effected by perforating the polyolefin material with the aid of water jets.

11. The absorbent article according to claim 1, wherein the density is 0.01–0.2 g/cm$^3$.

12. The absorbent article according to claim 1, wherein the density is 0.02–0.1 g/cm$^3$.

13. The absorbent article according to claim 1, wherein the foamed polyolefin material is polyethylene.

14. The absorbent article of claim 1, wherein the absorbent article is one of a diaper, sanitary napkin, tampon, panty protector, and an incontinence guard.

* * * * *